United States Patent [19]

Tateosian et al.

[11] Patent Number: 5,210,109

[45] Date of Patent: May 11, 1993

[54] INTERPENETRATING POLYMER NETWORK COMPOSITIONS EMPLOYING RUBBER-MODIFIED POLYMERS

[75] Inventors: Louis H. Tateosian; W. Donald Wilson, both of York, Pa.

[73] Assignee: Dentsply Research & Development Corp., Milford, Del.

[21] Appl. No.: 948,627

[22] Filed: Sep. 21, 1992

Related U.S. Application Data

[60] Continuation of Ser. No. 341,085, Apr. 20, 1989, abandoned, which is a division of Ser. No. 119,130, Nov. 10, 1987, Pat. No. 4,863,977, which is a division of Ser. No. 654,860, Sep. 25, 1984, Pat. No. 4,711,913, which is a continuation-in-part of Ser. No. 552,300, Nov. 16, 1983, Pat. No. 4,551,486.

[51] Int. Cl.$^5$ .................. C08F 2/50; C08F 291/00; C08K 9/06; C08L 31/06
[52] U.S. Cl. ........................ 522/14; 522/18; 522/28; 522/95; 522/110; 523/109; 523/115; 523/116; 523/206; 523/212; 524/456; 524/493; 524/504; 525/66; 525/77; 525/82; 525/86; 525/92; 525/95; 525/902; 525/903
[58] Field of Search .................. 522/14, 18, 28, 110, 522/95; 523/109, 115, 116, 206, 212, 903; 524/456, 493, 504; 525/66, 77, 82, 86, 92, 95, 902

[56] References Cited

U.S. PATENT DOCUMENTS

| | | |
|---|---|---|
| 2,673,194 | 11/1951 | Grim . |
| 3,427,274 | 2/1969 | Cornell . |
| 3,470,615 | 10/1969 | Petner . |
| 3,589,385 | 6/1971 | Vitous . |
| 3,647,498 | 3/1972 | Dougherty . |
| 3,808,687 | 5/1974 | Millet . |
| 3,887,652 | 6/1975 | Carrock . |
| 3,922,321 | 11/1975 | Yusa et al. . |
| 4,035,453 | 7/1977 | Hittmair et al. . |
| 4,071,424 | 1/1978 | Dart . |
| 4,078,018 | 3/1978 | Chauvel et al. . |
| 4,115,922 | 9/1978 | Alderman . |
| 4,125,700 | 11/1978 | Graham . |

(List continued on next page.)

FOREIGN PATENT DOCUMENTS

| | | |
|---|---|---|
| 239216 | 6/1962 | Australia . |
| 1196130 | 10/1985 | Canada . |
| 0011734 | 11/1979 | European Pat. Off. . |
| 0044352 | 7/1980 | European Pat. Off. . |
| 0053442 | 11/1981 | European Pat. Off. . |
| 0059525 | 7/1982 | European Pat. Off. . |
| 0070634 | 1/1983 | European Pat. Off. . |
| 0083446 | 7/1983 | European Pat. Off. . |
| 0142747 | 10/1984 | European Pat. Off. . |
| 1293791 | 10/1972 | United Kingdom . |
| 2074590 | 11/1981 | United Kingdom . |

OTHER PUBLICATIONS

Removable Prosthodontics, Johnston et al, vol. 43, No. 5, (Nov. 1981).

Macromolecules by L. H. Sperling et al, vol. 9, Nos. 4 and 5 (1976).

J. Polymer Science by L. H. Sperling et al, vol. 12, p. 141 (1977), and vol. 16, p. 583, (1978).

J. Elastoplast by Klempner et al, vol. 5, p. 196, (1970).

Primary Examiner—Herbert J. Lilling
Attorney, Agent, or Firm—Dale R. Lovercheck; Edward J. Hanson, Jr.

[57] ABSTRACT

This invention provides hardenable compositions useful as construction media for a wide range of applications. Particular utility is found in the dental and medical arts where such compositions are highly suitable for the formation and construction of denture base, denture baseplates, denture liners, denture repair, custom trays, veneering for crowns and bridgework, artificial teeth, veneers and repair for natural teeth, and tooth restorative fillings. Such materials having improved impact strengths and elastic moduli when hardened are disclosed which include rubber-modified polymer.

35 Claims, No Drawings

U.S. PATENT DOCUMENTS

| | | |
|---|---|---|
| 4,222,983 | 9/1980 | August et al. . |
| 4,243,793 | 1/1981 | Williams . |
| 4,267,133 | 6/1981 | Kohmura . |
| 4,281,991 | 8/1981 | Michl . |
| 4,288,221 | 9/1981 | Engel . |
| 4,297,185 | 10/1981 | Chevreux et al. . |
| 4,308,190 | 12/1981 | Walkowiak et al. . |
| 4,323,348 | 4/1982 | Schmitz-Josten et al. . |
| 4,341,883 | 7/1982 | Gift . |
| 4,351,853 | 9/1982 | Jochum . |
| 4,369,262 | 1/1983 | Walkowiak et al. . |
| 4,379,695 | 4/1983 | Orlowski et al. . |
| 4,383,826 | 5/1983 | Butler et al. . |
| 4,386,912 | 6/1983 | Nagase et al. . |
| 4,389,497 | 6/1983 | Schmitt et al. . |
| 4,394,465 | 7/1983 | Podszin et al. . |
| 4,396,377 | 8/1983 | Roemer et al. . |
| 4,396,476 | 8/1983 | Roemer et al. . |
| 4,433,103 | 2/1984 | Kamata et al. . |
| 4,442,240 | 4/1984 | Suh . |
| 4,454,258 | 6/1984 | Kawahara et al. . |
| 4,542,185 | 9/1985 | Meunier . |
| 4,551,486 | 11/1985 | Tateosian et al. . |
| 4,563,153 | 1/1986 | Schaefer . |
| 4,564,653 | 1/1986 | Kamata et al. . |
| 4,689,015 | 8/1987 | Denyer et al. . |
| 4,698,373 | 10/1987 | Tateosian et al. . |
| 4,711,913 | 12/1987 | Tateosian et al. . |
| 4,863,977 | 9/1989 | Tateosian et al. . |

INTERPENETRATING POLYMER NETWORK COMPOSITIONS EMPLOYING RUBBER-MODIFIED POLYMERS

CROSS-REFERENCE TO RELATED APPLICATIONS

This is a continuation of U.S. Ser. No. 07/341,085 filed Apr. 20, 1989, now abandoned, which is a division of U.S. Ser. No. 07/119,130 filed Nov. 10, 1987, now U.S. Pat. No. 4,863,977, which is a division of U.S. Ser. No. 06/654,860 filed Sep. 25, 1984, now U.S. Pat. No. 4,711,913, which is a continuation-in-part of U.S. Ser. No. 06/552,300 filed Nov. 16, 1983, now U.S. Pat. No. 4,551,486.

BACKGROUND OF THE INVENTION

This invention provides hardenable compositions useful as construction media for a wide range of applications. Particular utility is found in the dental and medical arts where such compositions are highly suitable for the formation and construction of denture base, denture baseplates, denture liners, denture repair, custom trays, veneering for crowns and bridgework, artificial teeth, veneers and repair for natural teeth, and tooth restorative fillings.

More particularly, the invention relates to polymeric compositions comprising one or more multifunctional crosslinking oligomers capable of addition polymerization, rubber-modified polymer, and optionally, inorganic filler, crosslinked polymers swellable in the oligomers and monofunctional monomers which form composite blends. The blends are tractable and are capable of being formed or molded and caused to polymerize to provide articles possessing superior physical and physiochemical properties including high impact strength and desirable elastic moduli.

This invention is also directed to methods for forming tractable, polymerizable blends through careful control of blending conditions including temperature, time, and effective pressure.

DESCRIPTION OF THE PREFERRED EMBODIMENTS

In general, the novel compositions of this invention are useful as the formation and construction media for a wide range of applications where custom-shaped articles are required without the use of a mold. Alternatively, low cost molds, that need not withstand heat or more than moderate pressure, may be used to form such shaped articles. These compositions are particularly useful with dental and medical arts in the formation and construction of denture base, denture baseplates, cranial and bone prostheses, denture liners, denture repair, custom trays, veneering for crowns and bridgework, artificial teeth, veneers and repair for natural teeth, and tooth restorative fillings.

In accordance with a preferred form of the present invention, hardenable dental compositions are provided which may easily and conveniently be molded and shaped by hand by known techniques into prosthetic dental appliances possessing chemical and physical properties which are significantly improved over those of conventional prior art acrylic dental appliances.

Briefly stated, the hardenable dental compositions of the invention comprise a blend of components which, when combined in certain proportions and permitted to age or mature, produce a blend that is moldable into prosthetic dentures and other dental devices. The blend is formed in accordance with certain embodiments of the invention by combining a crosslinked polymer, crosslinking oligomers capable of addition polymerization, and an inorganic filler and/or an initiator and/or a monofunctional monomer, and by allowing said combination to age or mature. The crosslinked polymer is in the form of discrete particles having average diameters ranging from about 0.001 micron to about 500 microns. Preferably, at least 50 percent by weight of said particles have diameters less than about 150 microns, and more preferably, less than 100 microns. If desired, a mixture of two or more different crosslinked polymers may be used. A characteristic of the crosslinked polymer is that it will be insoluble in, but will be swollen by the liquid components used in the preparation of the blend.

The liquid polymerizable component of the compositions of the invention is one or more multifunctional oligomers having the capacity to swell the particles of crosslinked polymer used in the practice of the invention.

It has been discovered that the relative proportions of the components of the blend produced in accordance with the invention are critical in preferred embodiments to the attainment of the desired properties in the unhardened state including slump resistance, packability, freedom from tackiness, penetration, flow, viscosity stability, and modelability. Also, the relative proportions of components are critical to the attainment of the desired properties in the final hardened or cured product produced therefrom, notably flexural fatigue, transverse strength, wear resistance, impact resistance, resistance to solvents, stain resistance, thermal stability, and hydrolytic stability. Thus, it has been discovered that blends of from about 10 to about 70 weight percent of the crosslinked polymer, from about 10 to about 70 weight percent of multifunctional oligomers, from about 3 to about 80 weight percent of inorganic filler, and less than about 2 weight percent of polymerizable monomer, together with minor amounts of initiator and in some cases activator or accelerator for the initiator, provide blends which are particularly useful in the production of denture bases characterized by properties far superior to those of conventional systems now used in the art.

Preferably, the multifunctional vinyl crosslinking composition or agent or multifunctional crosslinking oligomer capable of addition polymerization is preferably present in an amount of 10 to 70 weight percent, more preferably 20 to 60, and most preferably 30 to 65 weight percent. Preferably, the crosslinked polymer in the form of discrete particles is present in an amount of 3 to 70 weight percent, more preferably 5 to 70, and most preferably 8 to 55 weight percent. The inorganic filler is preferably present in the amount of 3 to 80 weight percent, more preferably 5 to 50, and most preferably 8 to 30 weight percent. The most preferred ranges are especially preferred for the preferred denture base composition, but not in general for some of the other aspects of the present invention.

Surprisingly, it has been found that in the composition of the present invention, the addition of silane monomer to the composition gives a special and advantageous effect on the strength and integrity of the cured composition. Especially the flexural fatigue and transverse strength are greatly enhanced by blending the silane into the composition The characteristics of the homogeneity of the filler distribution throughout the composite composition are also enhanced. The physical mixing process is also made easier and faster. (Gamma)-methacryloxypropyl trimethoxysilane is soluble in the composition of the present invention prior to curing or polymerization and gives excellent results. Any vinyl functional silane having proper solution characteristics is preferred, and especially preferred are the acrylic functional silanes The silane is preferably included in the composition in an amount of 0.001 to 2 weight percent, more preferably 0.01 to 1.5 weight percent, and most preferably 0.05 to 1 weight percent.

In general, the crosslinked polymers which are useful in the practice of the invention are formed from monomers or blends of monomers together with crosslinking agents in proper proportion. The monomers suitable for use in the production of the crosslinked polymers useful in the practice of the invention will generally comprise any of a wide variety of monomers such as, for example, acrylic and lower alkyl acrylic acid esters, N-vinyl lactams, acrylamides, acrylonitriles, styrenes, alkenes, and urethanes. Similarly, mixtures of two or more monomers may be employed to provide these crosslinked polymers.

Preferred monomeric species useful in the preparation of the crosslinked polymers of the invention include acrylic and lower alkyl acrylic acid esters which generally conform to the structure:

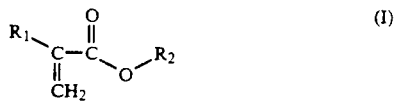

(I)

where $R_1$ is hydrogen or an alkyl group including from 1 to about 6 carbon atoms, and where $R_2$ is either (a) an alkyl or cycloalkyl group including from 1 to about 20, and preferably from 1 to about 6 carbon atoms; (b) phenyl; and (c) substituted phenyl in which the alkyl groups include from 1 to about 6 carbon atoms Various substituents may be present on either or both of the groups $R_1$ and $R_2$. Thus, hydroxyl, amino, thiol, and halogen (e.g., fluorine, chlorine, etc.) functionalities may be present, with the latter being preferred. Fluorine is an especially suitable and useful substituent.

Especially preferred examples of monomers useful in the production of the crosslinked polymers used in the practice of the invention include methyl-, ethyl-, isopropyl-, tertbutyl-, octyl-, dodecyl-, cyclohexyl-, chloromethyl-, tetrachloroethyl-, perfluorooctyl-, hydroxyethyl-, hydroxypropyl-, hydroxybutyl-, 3-hydroxyphenyl-, 4-hydroxyphenyl-, aminoethyl-, aminophenyl-, and thiophenyl-, acrylate, methacrylate, ethacrylate, propacrylate, butacrylate, and chloromethacrylate, as well as the homologous mono-acrylic acid esters of bisphenol-A, dihydroxydiphenyl sulfoxide, and 2,2 bis (4-hydroxy-2,3,5,6-tetrafluorophenyl) propane. Other suitable species will be apparent to those skilled in the art. If desired, mixtures of two or more different monomers may be used to provide the crosslinked polymers useful in the practice of the invention.

The crosslinking agents which are useful in the production of the crosslinked polymer component of the invention comprise a wide variety of di- or polyfunctional moieties which are capable of crosslinking. In general, the reactive functionalities which serve as active sites for such crosslinking are ethylenic functions, but other reactive and effective crosslinking functions are similarly useful as will be hereinafter described. The use of crosslinking agents in the formulation of polymers is well known to those skilled in the art, who similarly recognize that it is necessary for such agents to have at least two reactive functionalities.

Suitable crosslinking agents may be selected from numerous families of polyfunctional monomers such as acrylic and lower alkyl acrylic acid diesters, acrylic and lower alkyl acrylic acid esters formed from alcohols, which alcohols have a second reactive function, urethane diacrylates and dimethacrylates, polyvinylic compounds, divinyl aromatic compounds and others, as will be apparent to those skilled in the art.

Preferably, the crosslinking agents comprise esters of unsaturated acids, e.g., acrylic, methacrylic, ethacrylic, propacrylic, butacrylic, etc., maleic, fumaric, citraconic, mesaconic, itaconic, malonic, or aconitic, etc., acids. Other unsaturated acids will be readily apparent to those skilled in the art. These acids are preferably reacted with either unsaturated or polyhydroxylic alcohols to form esters which are effective polyfunctional crosslinking agents useful in the formulation of the crosslinked polymers of the invention. In general, these alcohols have one or more hydroxylic functionalities and have from 2 to about 30 carbon atoms. Thus, useful alcohols include allyl, methallyl, crotyl, vinyl, butenyl, isobutenyl, and similar unsaturated alcohols as well as polyols such as ethylene glycol, propylene glycol, butylene glycol, diethylene glycol, triethylene glycol, tetraethylene glycol, pentaethylene glycol, glycerol, 1,3,3-trimethylolpropane, pentaerythritol, dihydroxyphenol, and alkylidene bisphenols such as bisphenol-A, 1,1-bis(4-hydroxyphenyl)methane, 4,4'-dihydroxybiphenyl, 4,4'-dihydroxydiphenyl sulfone, dihydroxydiphenyl ether, dihydroxydiphenyl sulfoxide, resorcinol, hydroquinone, etc.

Crosslinking agents preferred for the practice of the invention include the esters of a mono- or dibasic unsaturated acid with an unsaturated monohydroxylic alcohol such as allyl acrylate, allyl methacrylate, vinyl acrylate (methacrylate and $C_1$ to $C_{20}$ homologs), dimethallyl fumarate, N-allyl acrylamide, crotyl acrylate, allyl crotonate, allyl cinnamate, diallyl maleate, etc. Other preferred species are the di-, tri, and higher esters of polyhydroxylic alcohols such as ethylene "glycol" diacrylate (dimethacrylate and $C_2$–$C_4O$ homologs), trimethylolpropane trimethacrylate, and the diacrylate and dimethacrylate esters of bisphenol-A as well as acrylate and alkyl acrylate esters which correspond to the general formula:

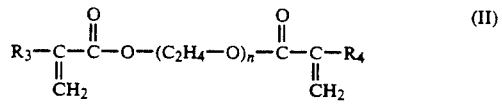

(II)

where $R_3$ and $R_4$ may be the same or different and are hydrogen or alkyl groups containing from 1 to about 6 carbon atoms and n is a whole number from 1 to about 10. Alternatively, the crosslinking agent may conform to the formula

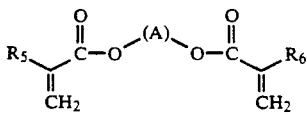

(III)

where $R_5$ and $R_6$ may be the same or different and are hydrogen or alkyl groups containing from 1 to about 6 carbon atoms and A is an aromatic moiety selected from the group consisting of (a) biphenyl, diphenyl alkylidene having from 1 to about 6 carbon atoms in the alkylidene portion thereof, diphenyl sulfone, diphenyl sulfoxide, diphenyl ether, and diphenyl sulfide; (b) the diglycidyl derivatives of group (a); and (c) the diurethane derivative of either group (a) or group (b). In addition, the crosslinking agent may be a glycidyl acrylate or allyl acrylate, divinyl (trivinyl or higher homologs) benzene, substituted divinyl benzenes, and analogous compounds. Furthermore, mixtures of two or more crosslinking agents are useful in the practice of the invention.

Compounds such as bis-GMA and the urethane diacrylates formed by reacting hydroxyethyl acrylate, hydroxypropyl acrylate, and their methacrylic homologs with 2,2,4-trimethylhexyl-1,6-diisocyanate are especially useful, as are diallyl maleate, ethylene "glycol" dimethacrylate, trimethylolpropane trimethacrylate and the dimethacrylate ester of bisphenol-A.

The crosslinked polymers are produced by polymerizing a mixture of the monomer or monomers and crosslinking agent or agents described above. The amount of crosslinking agent employed in the production of the crosslinked polymers used in the practice of the invention is a critical factor. It has been found that the capacity of particles of polymers so produced to swell with or to imbibe the liquid components forming the compositions of the invention, is directly related to the amount of crosslinking agent used in the production of such crosslinked polymers.

The physiochemical properties of the crosslinked polymers useful in the practice of the invention determine the relative proportions of monomer and crosslinking agent used to formulate said suitable crosslinked polymers. Such crosslinked polymers must be sufficiently well crosslinked as to maintain substantially their structural identity when exposed to the liquid components of the compositions of the invention. At the same time, they must not be so thoroughly crosslinked as to be incapable of swelling with or imbibing such liquid components. Thus, it is convenient to describe the proportion of crosslinking agent by what it does rather than by what it is. In view of the fact that the crosslinked polymers are utilized in finely particulate form, as will be more fully explained, it is convenient to define the minimum amount of crosslinking agent used therein as being that amount which is sufficient to cause the particulate crosslinked polymer not to lose its particulate discreteness upon exposure to the liquid components of the invention. Similarly, the maximum amount of crosslinking agent used therein is that amount beyond which the resulting crosslinked polymer particles are unable to swell with or further imbibe a significant portion of liquid components upon exposure thereto. In this regard, a quantity of crosslinked polymer particles would be said to swell with or imbibe a significant portion of liquid components if it swelled with or has imbibed at least 10 percent of its own weight of such liquid. Preferably, an amount of crosslinking agent is used to provide a crosslinked polymer having the capacity to imbibe from about 10 to about 500 percent of its own weight of liquid components.

It will be clear to those skilled in the art that the minimum and maximum values for the proportions of crosslinking agents suitable for inclusion in the crosslinked polymers of this invention will vary depending upon the chemical identity of the component monomers and crosslinking agents. In general, however, the crosslinking agents may comprise from as low as about 0.01 percent to as high as about 30 percent, preferably from about 0.02 percent to about 5 percent, and more preferably from about 0.05 percent to about 1.5 percent by weight of the resulting crosslinked polymer.

The production of the crosslinked polymers useful in the practice of this invention from monomers and crosslinking agents may be performed by any of the many processes known to those skilled in the art. Thus, the polymers may be formed by heating a mixture of the components to a temperature sufficient to cause polymerization, either with or without the addition of initiators. For this purpose, peroxy type initiators such as benzoyl peroxide, dicumyl peroxide, and other materials familiar to those skilled in the art may be employed, and the use of activators may be advantageous in some formulations. Alternatively, the crosslinked polymers of the invention may be formed from the constituents by photochemical or radiant initiation utilizing light or high energy radiation. For photochemical initiation, photochexical sensitizers, or energy transfer compounds may be employed to enhance the overall polymerization efficiency in manners well known to those skilled in the art.

The polymerization of the crosslinked polymers may be accomplished in a wide variety of ways, all of which are known to those skilled in the art. Thus, they may be formed by suspension polymerization as taught in U.S. Pat. No. 2,673,194 to Grim, emulsion polymerization, block polymerization, or any other useful and convenient process. Since, as will be more fully described herein, it is desirable to have the crosslinked polymer available in the form of finely particulated granules or beads, suspension polymerization is especially convenient. Blocks of bulk-formed polymer may be crushed to yield a useful product, however. The size of the particles of crosslinked polymer is of significance to the invention. As indicated, it is desirable that the crosslinked polymer be in the form of small, discrete particles or beads. The average particle size should be from about 0.001 micron to about 500 microns. It is preferred that at least 50 percent by weight of the particles have diameters below 150 microns and more preferably below 100 microns.

The multifunctional crosslinking oligomers and/or monomers useful in the practice of the invention comprise a wide variety of di- or polyfunctional moieties which are capable of addition polymerization. In general, the reactive functionalities which serve as active sites for this polymerization are ethylenic functions, e.g. acrylic, vinyl alkyl, and other reactive groups are similarly useful. The use of multifunctional oligomers and monomers in the formulation and elaboration of polymeric composites is well known to those skilled in the art, who will appreciate that it is necessary for such agents to have at least two reactive functionalities and to therefore be multifunctioned. Suitable multifunctional monomers and oligomers may be selected from numerous families of polyfunctional vinyl and/or addition polymerizable monomers such as acrylic and lower alkyl acrylic acid diesters, acrylic and lower alkyl acrylic acid esters formed from alcohols, which alcohols have a second reactive function, urethane diacrylates and dimethacrylates, polyvinylic compounds, divinyl aromatic compounds, and others as will be apparent to those skilled in the art.

Preferably, the multifunctional monomers and oligomers comprise esters of unsaturated acids, e.g., acrylic, methacrylic, ethacrylic, propacrylic, butacrylic, maleic, fumaric, citraconic, mesaconic, itaconic, malonic, or aconitic, etc., acids. Other unsaturated acids will be readily apparent to those skilled in the art. These acids are preferably reacted with either unsaturated or polyhydroxylic alcohols to form esters which are effective multifunctional monomers and oligomers useful in the formulation of the compositions of the invention. In general, these alcohols have one or more hydroxylic functionality and have from 2 to about 30 carbon atoms. Thus, useful alcohols include allyl, methallyl, crotyl, vinyl, butenyl, isobutenyl, and similar unsaturated alcohols as well as polyols such as ethylene glycol, propylene glycol, butylene glycol, diethylene glycol, triethylene glycol, tetraethylene glycol, pentaethylene glycol, glycerol, 1,3,3-trimethylol-propane, pentaerythritol, dihydroxyphenol, and alkylidene bisphenols such as bisphenol-A, 1,1-bis (4-hydroxyphenyl) methane, 4,4'-dihydroxybiphenyl, 4,4'-dihydroxydiphenyl sulfone, dihydroxydiphenyl ether, dihydroxydiphenyl sulfoxide, resorcinol, hydroquinone, etc.

The preferred multifunctional monomers and oligomers used in the practice of the invention include the esters of a monomeric dibasic unsaturated acid with an unsaturated mono-hydroxylic alcohol such as allyl acrylate, allyl methacrylate, vinyl acrylate (methacrylate homologs), dimethallyl fumarate, N-allyl acrylamide, crotyl acrylate, allyl crotonate, allyl cinnamate, diallyl maleate, etc. Other preferred species are the di-, tri-, and higher esters of polyhydroxylic alcohols such as ethylene "glycol" diacrylate (dimethacrylate and $C_2$–$C_6$ homologs), trimethylolpropane trimethacrylate, and the dimethacrylate ester of bisphenol-A as well as other acrylate and alkyl acrylate esters corresponding to Formula II, above. Alternatively, the multifunctional monomers and/or oligomers may conform to Formula III, above. In addition, the multifunctional monomers and/or oligomers for the glycidyl acrylate or allyl acrylate, divinyl (trivinyl or higher homologs) benzene, substituted divinyl benzenes, or analogous compounds. Furthermore, mixtures of crosslinking agents are useful in the practice of the invention.

Compounds such as bis-GMA and the urethane dimethacrylate formed from the reaction of hydroxyethyl acrylate, hydroxypropyl acrylate, and their methacrylate homologs with 2,2,4-trimethylhexyl-1,6-diisocyanate (hereinafter referred to as "urethane dimethacrylate" or "diacrylate") are especially useful, as are ethylene "glycol" dimethacrylate, 1,6-hexanediol dimethacrylate trimethylolpropane trimethacrylate and the dimethacrylate ester of bisphenol-A and urethane adducts thereof. The corresponding acrylates are similarly useful as is diallyl maleate.

In addition to the components described above, (i.e., crosslinked polymer, filler, and a crosslinking agent) the blend further may contain additional, optional ingredients. These may comprise initiators, activators, pigments, radiopaquing agents, adhesion modifiers, and other materials as will occur to those skilled in the art.

The blends of the invention are formulated by a mixing together of the constituent species in proper proportion, followed by aging or maturing. Several techniques are available for this and others will be apparent to those skilled in the art. Thus, it is possible to combine crosslinked polymer, filler, and a crosslinking agent in proper proportions including therewith, for example, a peroxide initiator, and a pigment. This combination is then thoroughly mixed and aged to result in a blend which has a uniform appearance.

It is understood, however, that the blends are suitable for a very wide range of dental uses, including fillings, teeth, bridges, crowns, veneers, facings, pit and fissure sealants, denture base and denture reline materials, orthodontic splint materials, and adhesives for orthodontic appliances. The materials of the invention may also be utilized for prosthetic replacement or repair of various hard body structures such as bone and may be utilized for reconstructive purposes during surgery, especially oral surgery. They are also useful for various non-dental uses as, for example, in plastic construction materials.

The nature of the chemical and physical relationships among the components of the blends of the invention is important to the practice of the invention. Chief among these relationships is the necessity that the crosslinked polymer particles be capable of swelling with or imbibing the liquid components of the invention. In accordance with the invention, the blend formed by any of the useful techniques described above is aged for a period of time sufficient to insure that the crosslinked polymer has become substantially fully swollen with, interpenetrated by or has substantially imbibed the crosslinking agent. Thus, as used herein, "aged" or "aging" refers to the maintenance of the components of the blend in association with one another in the blend for a period of time sufficient to substantially fully swell the crosslinked polymer particles with the crosslinking agent. Frequently, the aging process is manifested by a change in the consistency of the blend as equilibrium is approached. The time necessary to approach such equilibrium will vary depending upon the blending techniques, the relative proportions of materials, the particle sizes and molecular weights of the polymer, and the temperature extent in the blend. In general, aging time of from one to seven days has been found to be adequate to approach the desired equilibrium. It is to be understood that it lies well within the abilities of those skilled in the art to ascertain the optimum aging time for a formulation in view of the foregoing considerations.

Upon polymerization of the blends, a three dimensional structure is believed to be formed which may be denominated as an interpenetrating polymeric network. The structure which is thought thus to form is believed to be a major contributing factor to the serendipitous combination of superior chemical and physiochemical properties which is exhibited by the articles constructed according to the practice of the invention. Interpenetrating polymeric networks are related to, but distinct from, traditional graft polymers. In general, when a second polymer is synthesized in the intimate presence of a first polymer, the resultant material has been known as a graft polymer regardless of the actual extent of chemical grafting of one polymer to the other. Interpenetrating polymer networks are thought to be formed, however, when the first polymer is substantially crosslinked into a three dimensional network prior to the formation of the second polymer, and when that second polymer is caused to form in such a fashion that it too is substantially crosslinked into a three dimensional network. Such network may also "suspend" inclusions of inorganic origin such as, for example, pigments and fillers.

Thus, an interpenetrating polymeric network may be viewed as being composed of two or more crosslinked, and hence three dimensionally arrayed, polymeric networks which co-exist in the same volume of space, but which do not necessarily have any covalent bonds in common. While the two networks may, indeed, be independent in the sense that they need possess no covalent linkages between them, they are physically trapped one "within" the other and cannot disassociate by any physical manipulation without the rupture of covalent bonds.

Central to an understanding of interpenetrating polymeric networks is the recognition that an interpentrating polymeric network is not a substance per se, but is, rather, a term descriptive of a structure. For discussions of the nature of interpenetrating polymeric network's in general, see the recent papers by L. H. Sperling et al, *Macromolecules*, volume 9, No. 4 (1976); *Macromolecules*, volume 9, No. 5 (1976); *J Polymer Science*, volume 12, page 141 (1977); and *J Polymer Science*, volume 16, page 583 (1978); and articles cited therein. Also, see Klepner et al, *J Elastoplast*, volume 5, page 196 (October 1973).

While it appears to be desirable that the crosslinking of both polymers be substantial, various degrees of crosslinking are possible in both the preformed polymer and the polymer formed in situ. In addition, it should be recognized that an interpenetrating polymeric network may be formed even when the initial and second polymers are formed from the same materials. For example, two independent networks of a polymethacrylate, suitably crosslinked, may interpenetrate each other to form an interpenetrating polymeric network. Similarly, an interpenetrating polymeric network need not be limited only to two networks, as mixtures of two or more polymers may be used as the polymer. Mixtures of two or more crosslinking agents may also be used in network formation.

It is thought that in the present invention, interpenetrating polymeric networks may be formed. Thus, when particulate crosslinked polymer is allowed to swell with or imbibe crosslinking agent, and when the imbibed crosslinking agent is subsequently caused to polymerize, an interpenetrating polymeric network may be seen to be formed within the confines of the particulate crosslinked polymer. It is believed that it is this interpenetrating polymeric network structure, which is localized in the particulate masses formed subsequent to the swelling of particulate crosslinked polymer and the polymerization of the blend, that lends the superior chemical and physiochemical properties to the articles formed according to this invention. It is believed that the aging process employed in the preparation of the precursor blends of the invention is required to accomplish substantially full swelling with interpenetration by or substantially complete imbibition of crosslinking agent by the crosslinked polymer particles, and to approach an equilibrium thereof. It is to be understood, however, that the foregoing discussion of interpenetrating polymeric networks and their application to the present invention is not to be construed as a limiting factor thereof, but, rather, is to be interpreted as a mechanism which is proposed as being applicable in the present case.

As has been indicated, the compositions of the invention exhibit superior chemical and physiochemical properties. Accordingly, the articles made from the compositions of the invention exhibit flexural fatigue, transverse strength, impact, and chemical resistance as denture bases. In addition, such articles display a unique microstructure.

The invention has, as another important feature, the inclusion of inorganic filler. Included in the inorganic fillers are the especially preferred silicious fillers. Especially preferred are the inorganic glasses. Among these are barium aluminum silicate, lithium aluminum silicate, strontium, lanthanum, tantalum aluminosilicate glasses, and related materials. Glass beads, silica, especially in submicron sizes, quartz, borosilicates, and other fillers may also be employed. Such fillers may be silanated prior to use in the adhesives of this invention. Silanation is well known to those skilled in the art and any silanating compound known to them may be used for this purpose.

Especially preferred is silanated microfine amorphous silicone dioxide particulate. Silanated means that some of the silanol groups have been substituted or reacted with, for example, dimethyldiclorosilane to form a hydrophobic filler. The particles are typically from 50 to 95 percent silanated. Silanated inorganic fillers are considered for purposes of this invention to be inorganic fillers.

In accordance with certain, preferred embodiments of the instant invention, it is desired to improve the impact strength of hardened compositions which may be formed hereby. In addition, it is frequently preferred to prepare materials having improved flexural strength and the ability to be reversibly deformed under applied load. In this regard, one of ordinary skill in the art will appreciate that in the preparation of certain articles such as denture baseplates and the like, it is frequently necessary to remove a hardened, shaped portion of material from a rigid template prepared from a mouth impression or the like. In this regard, the presence of undercutting or of certain geometrical formations may make it necessary to deform slightly the hardened composition. It is greatly to be preferred, therefore, to provide materials which can be deformed in that context, and which exhibit impact and flexural strengths which are consistent with these uses and practices. This goal is attained in accordance with the present invention by including within the compositional blends from which the shaped articles are formed certain rubber-modified polymers.

Accordingly, it is a preferred embodiment to provide polymerizable compositions comprising from about 10 to about 70 weight percent of multifunctional crosslinking composition, and from about 3 to about 70 weight percent of polymer composition. The polymer composition is selected to comprise up to about 90 weight percent of crosslinked polymer in the form of discrete particles having average diameters up to about 500 microns and being swellable in the crosslinking composition. The polymer composition is also selected to comprise at least about 10, preferably at least about 20, and even more preferably at least about 30 percent by weight of the polymer composition of rubber-modified polymer. The rubber-modified polymer comprises particles of an elastomer having a glass transition temperature below about 0° C. and having average diameters less than about 5 microns, said particles being overpolymerized with from about 10% to about 80% by weight of monomeric species, said overpolymerized particles being preferably suspension polymerized with from about 80% to about 98% of monomeric species to form macroparticles of the rubber-modified polymer having average diameters less than about 200 microns.

The macroparticulate rubber-modified polymer is preferably present in the total polymerizable composition in amounts of at least about 3 weight percent, preferably at least about 10 weight percent and most preferably, at least about 30 weight percent of the total polymerizable composition. Preferably, the rubber-modified polymer is present in an amount of at least about 60% and even more preferably is present in amounts of greater than about 90% by weight of the polymer composition. In accordance with other embodiments, the composition may further comprise monofunctional, polymerizable composition in an amount sufficient to improve the swelling of crosslinked polymer particles which may be added to the polymerizable blend in the crosslinking composition and preferably includes up to about 80 weight percent of inorganic filler.

The multifunctional crosslinking composition, inorganic filler, particulate crosslinked polymer and monofunctional polymerizable composition have already been described hereinabove. In accordance with the present embodiment, it is preferred that the multifunctional crosslinking composition comprise from about 10 to about 70 weight percent of the polymerizable composition. It is more preferred that the multifunctional crosslinking composition comprise from about 20 to about 60 weight percent, and even more preferred that it comprise from about 30 to about 50 weight percent of the polymerizable composition. Inorganic filler is present in amounts up to about 80 weight percent of the polymerizable composition, preferably in amounts of about 3 to about 80 percent, 5 to about 70 weight percent thereof and even more preferably from about 8 to about 55 weight percent.

When present, the monofunctional polymerizable composition is present in an amount sufficient to improve the swelling of crosslinked polymer which may be included in the composition, in the crosslinking composition. This amount generally ranges from 0 to about 60 weight percent of the polymerizable composition. Preferably, monofunctional composition is present in an amount of from about 1 to about 40 weight percent and even more preferably in amounts of from about 5 to about 20 weight percent of the polymerizable composition.

The polymer composition may also include other polymers such as uncrosslinked polymers, oligomers, block copolymers, graft copolymers and other materials as may be appreciated by those of ordinary skill in the art.

The rubber-modified polymers of the instant embodiments preferably comprise particles of an elastomer having a glass transition temperature below about 0° C. and having average diameters less than about 5 microns. The elastomer particles are overpolymerized with from about 10% to about 80% by weight of monomeric species, said overpolymerized particles being subsequently suspension polymerized with from about 80% to about 98% of the same or of a different monomeric species to form macroparticles having average diameters less than about 200 microns.

The rubber-modified polymer is preferably selected as to composition and preferably included in an amount effective to permit polymerized articles to be formed from the composition having a Gardner impact value (ASTM-3029-72) greater than about 1.5 in-lbs, preferably more than about 2.5 in-lbs and even more preferably greater than about 3.5 in-lbs. The rubber-modified polymer is included preferably to provide improved elastic modulus (ASTM D-970-71) in the hardened compositions. Thus, moduli less than about 2 million psi, preferably less than about 1 million psi and even more preferably less than about 800,000 psi are preferably attained.

It is also desired that the hardened compositions have deflections at break values of more than about 1 mm, preferably 1.5 mm and even more preferably 2.5 mm according to ASTM D-790-71 when employing a 0.39×0.10×2.56 inch sample. It is believed that those of ordinary skill in the art will have no difficulty in identifying preferred rubber-modified polymers from these considerations.

The most preferred rubber-modified polymers for use in accordance with the instant invention are graft polymers which comprise copolymers of acrylic monomers on styrene-butadiene rubber latexes subsequently reacted with monomers into macroparticles.

The preferred styrene-butadiene latexes which are useful in the practice of the instant invention preferably comprise from about 60% to about 90% by weight of butadiene and from about 10% to about 40% by weight of styrene. It is more preferred that such materials comprise from about 50% to about 80% of butadiene. Other polymeric and copolymeric species may be included or substituted in these latexes including polymers and copolymers, acrylonitriles, isoprenes, urethanes, acrylates, methacrylates, and other species as will be appreciated by those of ordinary skill in the art. The elastomers to be employed in the practice of these embodiments of the invention are those having glass transition temperatures below about 0° C. and having average particulate diameters less than about 5 microns.

The particles of elastomeric latex are, in accordance with the present embodiments, overpolymerized with monomeric species, preferably acrylic-type monomers. Thus, monomers of acrylates, methacrylates and similar monomeric species are employed from about 10% to about 80% by weight of the total weight of the overpolymerized material. It is preferred that such overpolymerizing species comprise from about 15% to about 50% by weight of the overpolymerized elastomeric particles. In accordance with certain embodiments, the overpolymerizing species may also comprise up to about 5% of a multi-functional crosslinking species as hereinbefore described.

The overpolymerized elastomeric particles are subsequently suspension polymerized with from about 80% to about 98% by weight of monomeric species to form macroparticles having average diameters less than about 200 microns. It is preferred that the macroparticles comprise particles having average diameters between about 30 and 100 microns. The monomeric species which may be employed for the formation of macroparticles in this regard may be any of the polymerizable monomeric species hereinbefore described, but are, preferably, acrylic in nature. In accordance with certain embodiments, up to about 5% of a multifunctional crosslinking agent may be admixed with the monomeric species for the formation of macroparticles. They may be the same or different from the species employed to effect overpolymerization of the elastomer particles.

The procedures which are preferably employed in the formation of the macroparticles are described generally in U.S. Pat. No. 3,427,274—Cornell, which is incorporated herein by reference. Other procedures will be readily apparent to those of ordinary skill in the art.

In accordance with the present invention, it is particularly desired to employ actinic light curing systems to facilitate the hardening of articles shaped from the compositions. Exemplary systems are disclosed in U.S. Pat. No. 4,071,424—Dart et al., incorporated herein by reference, to provide additional disclosures for such systems. It is preferred to employ an alkyl, alpha diketone such as camphoroquinone together with an amine reducing agent in such systems.

In accordance with another embodiment of the instant invention, methods are provided for providing hard, shaped objects. As will be appreciated by those of ordinary skill in the art, it is important for the preparation of dental objects such as denture baseplates, prostheses and the like to have polymerizable materials which are smooth and uniform. It is even more important to have such materials which are tractable, that is, which are capable of being worked by hand in those manners which artisans commonly employ and which is not sticky, granular, frangible, resistive, or otherwise difficult to work. It is similarly desired that the materials not run or sag upon application, but that they conform evenly and truly to a modeled surface and remain stable during working. Accordingly, an embodiment of the instant invention is directed to preparing smooth, tractable and substantially uniform polymerizable compositions, to shaping of the polymerizable compositions into a shaped body such as a denture baseplate or prosthesis, and to effecting polymerization of the body to provide the desired hard, shaped object. Of course, it is also desired that such object have a Gardner impact value greater than about 1.5 in/lb. after hardening and an elastic modulus less than about 2,000,000 psi. This is accomplished by combining components comprising from about 10 to about 70 weight percent of multifunctional crosslinking composition, and from about 3 to about 70 weight percent of polymer composition as hereinbefore described together with a preferred polymerization initiation system. The polymer composition will comprise at least about 10 weight percent of rubber-modified polymer and up to about 90 weight percent of crosslinked polymer as hereinbefore described. Up to about 80 weight percent of inorganic filler may also be included. The foregoing components are blended at a temperature between about 30° C. and about 100° C. and at a pressure between about 50 and about 200 mm of mercury for a time sufficient to provide smooth, tractable, substantially uniform, polymerizable composition.

It has been found that the foregoing conditions of time, temperature and pressure are critical to the effectuation of the preparation of polymerizable materials which are at once smooth, substantially uniform, and tractable. In accordance with the preferred foregoing methods, the rubber-modified polymer is selected to have a Young's modulus and to be present in amounts which, taken in combination, are sufficient to provide resulting, hardened, shaped bodies with the desired Gardner impact and elastic modulus values and which are not inconsistent with the attainment of tractability in the polymerizable compositions.

It is a particular feature of the present invention to provide superior energy absorption facility in the end product. Accordingly, the multifunctional crosslinking composition has a relatively high molecular weight, preferably at least about 250, more preferably at least about 300, and most preferably greater than about 340. Such monomeric oligomers, as a class, may be generally described as providing longer polymer chains with high rates of polymerization and low shrinkage. The end product articles have improved physical properties as described above. The difficulty presented by this important feature is that such monomeric oligomers which are desired to swell the preferred polymer composition comprising polymerized particulates or beads swells the polymer composition only slowly or insufficiently at ambient operating temperatures.

It is therefore an important feature of the present invention in the practice of a preferred embodiment that the swellable polymer particles be swollen by the oligomer composition that forms the majority of the multifunctional crosslinking composition when held in admixture. It is also important that after said particles are swollen to an optimum extent, that they not swell excessively thereafter, so that a shelf-stable composition result. By not swelling, it is meant that substantially no visible swelling occurs, particularly as compared to the very substantial swelling that will occur at the preferred swelling temperatures that are a feature of the present embodiment.

The preferred temperatures for admixing and swelling or subsequent swelling after admixture of the particulate polymer by the polymerizable composition may for example be above about 39° C. and is at least about 35° to 80° C., preferably 40° to 75° C. and most preferably 45° to 70° C. The most preferred method is to combine all of the inredients and then mix them at the desired temperature for preferred periods of time which correlate in general at the preferred temperatures to less than about 4 hours, preferably less than 2 hours, and most preferably less than ¾ hour. Because there are many facility and equipment limitations and also in some instances, because of special properties, including problems of instability of the ingredients, it may be desired to mix the particulate polymer and polymerizable compositions and usually any other ingredients and then allow for swelling or additional swelling to a substantially equilibrium condition by maintaining the mixture without mixing under heat within the preferred temperature ranges given above for up to 96 hours, but more preferably for less than 48 hours and most preferably less than 24 hours. It is preferred that compositions in accordance with these embodiments be blended at a temperature of about 50° C. and at a pressure between about 30 mm and 100 mm of mercury.

In any event, it is important that a substantial plastisol be achieved and not a gel. Improper temperature or time of heating can result in the formation of a gel structure, and cause the resulting product to be not readily usable for fabricating dental articles. Another consequence of excessive temperature and/or time of processing is excessive prepolymerization of the polymerizable composition product before it has been converted into a shaped article such as a preferred dental article. Also, the typical inhibitors that are present in the system as a result of their typical presence in polymerizable starting materials are deleteriously effected by the heat in that they appear to be destroyed and may fail to function to stabilize the composition during storage.

In accordance with a preferred embodiment, the blending of the polymerizable composition takes place at a temperature of about 40° C. to about 70° C. and at a pressure above about 10 mm of mercury but less than about 150 mm mercury.

The invention is further illustrated by the following examples:

EXAMPLE 1

Organic Amine Salt Preparation

An organic amine salt was prepared from two feedstocks as follows:

332.1 g glacial methacrylic acid (MAA) and 5.7 g BHT were added to a two liter polyethylene bottle. The mixture was agitated until the BHT dissolved into a uniform solution. The MAA solution was then placed in a −12° C. freezer for four hours. The solution froze to a solid. At substantially the same time, about 700 g of dimethylaminoneopentyl acrylate (DMANPA) was added to a one liter polyethylene bottle and placed in the freezer for four hours. The DMANPA did not freeze and remained liquid.

Both bottles were removed from the freezer and 662.2 g of DMANPA were poured onto the frozen MAA solution. The combined MAA and DMANPA were mixed on a roller mill for one hour. The resulting amine salt DMANPA-MAA was a clear, slightly viscous liquid.

The Moldable Denture Base Compositions Preparation

A moldable denture base composition was formed that is hardenable with visible light. The denture base material was prepared according to the following formula:

| Percent by Weight of Total Composition | |
|---|---|
| 39.01 | Urethane dimethacrylate [N,N-bis (2-methacryloyloxyethoxycarbonyl)- 1,6-diamino-2,4,4-trimethylhexane which is the reaction product of hydroxyethyl methacrylate and 2,2,4-trimethylhexyl-1, 6-diisocyanate) |
| 2.54 | 1,6-Hexanediol dimethacrylate (HDDMA) |
| 0.13 | Camphoroquinone (CQ) |
| 0.66 | DMANPA-MAA salt |
| 42.48 | Poly (methyl methacrylate-co-ethylene dimethacrylate 99.8:0.2) a polymer supplied by L. D. Caulk Company* |
| 0.08 | Red acetate fibers |
| 0.02 | Pigments |
| 14.92 | Fumed silica inorganic filler (Aerosil R972, a product of Degussa) |
| 0.16 | Gamma-Methacryloxypropyltrimethoxysilane |

*The polymer was prepared according to the teaching of U.S. Pat. No. 4,396,476.

First, the CQ was dissolved in HDDMA and then mixed with the amine salt, the gamma methacryloxypropyltrimethoxysilane, and urethane dimethacrylate. The resulting liquid solution was charged to a double planetary mixer heated to 45° C. and mixed under 20 mm Hg pressure. Next, the polymer with the pigments and fibers previously blended in a V-Cone Blender was added and mixed under 20 mm pressure. The temperature was increased to 55° C. and the fumed silica was added in three increments of about equal size and mixed under 130 mm pressure each time. This produced a visible light curable (VLC) putty-paste.

The VLC putty was molded into a sheet 3.5 inches × 2.5 inches × 0.10 inches in a hydraulic press. The sheet was adapted as a baseplate to a stone model (coated with separator) made from an impression of the mouth. The baseplate was trimmed and then cured in two minutes on a turntable rotating under four 150 watt quartz-halogen lamps with a 400 to 500 nm band-pass filter. A preferred apparatus is shown in U.S. Ser. No. 492,284, filed May 6, 1983. The light flux varied from 100 to 130 mw/cm on the surface of the baseplate. Additional VLC putty was rolled into rope 0.25 inches in diameter. The rope was adapted around the ridge of the baseplate in a configuration to receive the pressed-in full arch of acrylic plastic teeth.

Bonding Agent Preparation

A bonding agent composition or adhesive tie coat was prepared by charging to a glass reactor the ingredients listed below in the proportions given and in the manner described below in a red light room.

| Percent By Weight | |
|---|---|
| 21.58 | Dicyclopentenyloxyethyl methacrylate (QM 657) Rohm and Haas Company |
| 4.32 | Acrylic Acid |
| 7.19 | 1,6-Hexanediol dimethacrylate (HDDMA) |
| 0.31 | Camphoroquinone (CQ) |
| 1.61 | Dimethylaminoneopentyl acrylate-methacrylic acid (DMANPA-MAA) salt* |
| 19.66 | Methymethacrylate (MMA) |
| 45.33 | Acrylated urethane oligomer (Uvithane 782, Morton-Thiokol Corporation) |

*DMANPA-MAA salt comprising 53.21 g DMANPA, 26.73 g MAA, 0.46 g BHT prepared as described in following organic amine salt preparation procedure.

The CQ was dissolved in the HDDMA an then added to the reactor. Next, the acrylic acid, DMANPA-MAA, QM657, and MAA were added with stirring. Finally, the Uvithane 782, previously heated to 60° C. for three hours, was added to the mixture with stirring. The mixture was stirred for 2.5 hours. A visually uniform, clear, solution was obtained. The solution was transferred to light proof bottles.

Bonding Procedure

A set of arch form teeth was formed according to the teaching of U.S. Ser. No. 510,405, filed Jul. 1, 1983 and assigned to the same assignee as the present application, the contents of which application are incorporated herein by reference, using the teaching of U.S. Pat. No. 4,396,377 previously referred to in this application.

The bonding agent composition formulated was applied as a visually thorough and complete covering to the ridge lap areas and about 2 mm onto the facial, lingual collar and interproximal areas of full arch upper teeth by applying with a brush. The bonding agent was bench set for two minutes and then light cured two minutes in the cure unit previously described.

The teeth coated with the bonding agent were then press-positioned in the rope of VLC putty. The teeth were then further trued in position in an articulator and then fixed in position by a two-minute light cure. Next, the facial and lingual aspects of the denture were finished with additional rope.

A liquid oxygen barrier coating described below was applied as a top coating before curing the visible light curable denture resin. The surface after photocuring for four minutes was dry, shiny, and tack free. The denture was then removed from the stone model and the other side of the denture was coated with the liquid oxygen barrier coating and then cured for two minutes under the light. The surface was dry, shiny, and tack free. Next, the cured denture was washed with tap water and dried with a paper towel. Both surfaces of the processed denture were shiny and tack free.

The oxygen barrier layer was prepared according to the following formulation:

| Percent By Weight | |
|---|---|
| 41.00 | Polyvinyl pyrrolidone (Plasdone K 29/32, GAF Corporation) |
| 58.23 | Water |
| 0.045 | Silicone antifoam (SAG 471, Union Carbide Corporation) |
| 0.225 | Surfactant (Makon 10, Stepan Chemical Corporation) |
| 0.50 | Potassium sorbate |

The above ingredients were mixed together at ambient conditions and the resulting solution was a very viscous clear yellow colored liquid with a viscosity of 850 centipoises at 22° C. (Brookfield #2 spindle, 20 rpm).

EXAMPLE 2

The following denture base composition was prepared and formed into a denture with excellent results according to the teaching of U.S. application Ser. No. 510,404, filed Jul. 1, 1983, which application is included by reference.

| Percent By Weight | |
|---|---|
| 39.44 | Urethane dimethacrylate (Reaction product of hydroxyethyl methacrylate and 2,2,4-trimethylhexyl-1,6-diisocyanate) |
| 2.57 | 1,6-Hexanediol dimethacrylate (HDDMA) |
| 0.13 | Camphoroquinone (CQ) |
| 0.59 | Reaction product of dimethylaminoethyl methacrylate and methacrylic acid (DMAEMA-MAA) |
| 42.10 | Poly (methyl methacrylate-co-ethylene dimethacrylate 99.8:0.2), a polymer supplied by L. D. Caulk Company (Polymer is in substantially spherical beads, the shape resulting from its suspension polymerization. At least 50 percent by weight of the beads have average diameters of less than 50 microns. The polymer was prepared from methyl methacrylate and ethylene dimethacrylate by suspension polymerization*). |
| 0.07 | Red acetate fibers |
| 0.03 | Pigments |
| 15.07 | Fumed silica inorganic filler (Aerosil R972, a product of DeGussa) |

*The polymer was prepared according to the teaching of U.S. Ser. No. 318,356, filed November 5, 1981, which was a continuation of U.S. Ser. No. 008,507, filed February 1, 1977.

First CQ was dissolved in HDDMA and then mixed with the DMAEMA-MAA and urethane dimethacrylate. The resulting liquid solution was charged to a double planetary mixer heated to 45° C. and mixed under 20 mm Hg pressure. Next, the polymer, pigments, and fibers were blended in a V-Cone Blender. The polymer blend was added and mixed under 20 mm pressure. The temperature was increased to 55° C. and the fumed silica was added in three increments of about equal size and mixed under mm pressure each time. This produced a visible light curable (VLC) putty-paste which is then further treated to remove excess entrapped air by placing the putty in a canister and subjecting it to 20 mm mercury pressure and then to high pressure in a hydraulic press. The putty was then extruded through Delrin Dies using a ram extruder into a sheet having a size of 0.1 inch × 2 5/8 inches and a rod having a diameter of 0.375 inch. The sheet and rod were then cut into lengths of about four inches.

By putty, it is meant a viscous material that can be deformed mechanically (manually) and will at least temporarily hold the shape into which it has been deformed or molded.

EXAMPLE 3

A restorative composition according to the present invention was compounded in a 1 quart Readco sigma blade mixer, heated at 55° C.:

| Weight % | Component |
|---|---|
| 61.30 | Silane treated microfine silica |
| 0.90 | Aerosil R972 TM (DeGussa) microfine silica filler |
| 7.10 | Suspension polymerized methyl methacrylate-co-ethylene dimethacrylate (99.8:0.2) |
| 27.60 | Reaction product of hydroxyethyl-methacrylate and 2,2,4-trimethylhexane-1,6-diisocyanate |
| 1.80 | 1,6-Hexanediol dimethacrylate |
| 0.95 | 3-Methacryloxypropyltrimethoxysilane |
| 0.09 | Camphoroquinone |
| 0.26 | Dimethylaminoethyl methacrylate |
| 0.003 | Pigments |
| Total 100.00% | |

The silane-treated microfine silica was prepared by silaning 1000 g OX50 fumed silica (DeGussa) with 200 g 3-methacryloxypropyltrimethoxysilane in 12 liters of hexane. The silica and 10 liters of hexane were stirred together for thirty minutes in a stainless steel bucket. Next, the silane was added and stirred for one hour. An additional 2 liters of hexane were added and the mixture was allowed to settle for sixteen hours. The mixture was decanted, filtered, washed with hexane, and dried at 115° C. for twenty-four hours. The resulting cake was broken up, milled, and sieved through a #10 screen.

The camphoroquinone, dimethylaminoethylmethacrylate, urethane dimethacrylate, and 1,6-hexanediol dixethacrylate were blended together and formed into a solution and then added to the mixer. The pigment was compounded with the polymer in a ball mill. The pigmented polymer was added, mixed with the liquid, and allowed to stand for twenty hours to form a preswell. The silanated silica and R972 silica were preblended and added in increments with stirring until a homogeneous mixture was obtained. Finally, the silane was added and mixed for thirty minutes. The resulting material is suitable for a posterior filling material, will deform a matrix band, and may be cured with the Prisma-Lite visible light polymerization unit to a hard solid. The composition of Example 3 did not discolor when placed and compacted with metallic amalgam placement and compacting instruments.

EXAMPLE 4

Modified Organic Amine Salt Preparation

An amine salt similar to that of Example 1 was prepared from a frozen blend of 15.5 g methacrylic acid, 9.0 g camphoroquinone and 0.9 g butylated hydroxy toluene to which was added 30.8 g of frozen dimethylaminoneopentyl acrylate. 11.7 g of 3-methacryloxypropyltrimethoxysilane was also added and the blend stirred to result in a clear solution.

Intermediate Composition
A V-cone blender was employed to blend the following:

| | |
|---|---|
| Rubber-modified polymer | 900.0 g. |
| Aerosil R-972 TM silica (Degussa Co.) | 300.0 g. |
| Red fiber concentrate: 2% red acetate fibers; 12% Aerosil R972; and 86% rubber modified polymer | 30.2 g. |
| Blue fiber concentrate: 2% blue acetate fibers; 12% Aerosil R972; and 86% rubber modified polymer | 1.1 g. |
| Scarlet pigment concentrate: 0.2% chromphtal scarlet RS; 2% Aerosil R972; and 97.8% rubber modified polymer | 25.2 g. |
| Yellow pigment concentrate: 0.2% yellow iron oxide; 2% Aerosil R972 and 97.8% rubber modified polymer | 3.1 g. |

The rubber modified polymer was prepared generally in accordance with Example 1 of U.S. Pat. No. 3,427,274—Cornell, incorporated herein by reference, by reacting an emulsion polymer of butadiene-styrene (70:30) overpolymerized with an equal amount of methyl methacrylate, with a blend of acrylic monomers comprising 93% by weight methyl methacrylate and 7% by weight butyl methacrylate by suspension polymerization in a 8.4:91.6 ratio.

Polymerizable Composition

A planetary mixer heated at 52° C. was charged with 294.13 g of N,N-bis-(2-methacryloyloxyethoxycarbonyl)-1,6-diamino-2,4,4-trimethylhexane (urethane dimethacrylate), and 5.87 g of the modified amine salt. The blend was deaerated while stirring. The intermediate composition, 250 g, was added, deaerated and mixed for 15 minutes. A second 250 g portion of intermediate was added, deaerated and mixed for 22 minutes under 85 mm Hg pressure. The resulting stiff paste was smooth, tractable, uniform and extrudable into sheet form. The material could be formed into a denture base as described generally in Example 1 and yielded a Gardner impact value of 4.4 in-lbs.

EXAMPLE 5

The method of Example 4 was repeated except that an emulsion polymer believed to contain a 75:25 ratio of butadiene to styrene was used and was overpolymerized in a ratio of 85:15 with methyl methacrylate. This polymer was reacted with methyl methacrylate and butyl methacrylate in a ratio of 10:90. The resulting rubber-co-modified polymer was employed in varying proportions with crosslinked particulate polymer poly (methyl methacrylate-co-ethylene dimethacrylate 99.8:0.2), hereinafter XL polymer, to form a polymer composition for addition to form the intermediate composition. The proportions of urethane dimethacrylate and R-972 silica were varied to some degree as well. The Gardner impact data and aesthetic observations follow:

| Run | Dimethacrylated Urethane | Rubber Modified Polymer | XL Polymer | R-972 | Gardner Impact Initial/16 hr @ 50° | Handleability |
|---|---|---|---|---|---|---|
| A. | 37.5% | 52.5% | 0% | 10% | — | intractable |
| B. | 54.5% | 34.1% | 0% | 11.4% | 2.6/3.9 | tractable |
| C. | 37.5% | 25.0% | 29.25% | 8.25% | 2.0/2.4 | tractable |
| D. | 37.5% | 20.0% | 35.8% | 6.7% | 1.6/2.4 | tractable |
| E. | 37.5% | 15.0% | 42.5% | 5.0% | 1.8/2.4 | tractable |
| F. | 37.5% | 10.0% | 42.5% | 10.0% | 1.3/2.4 | tractable |

EXAMPLE 6

The method of Example 4 was repeated using a polymer of 80:20 butadiene-styrene overpolymerized with methyl methacrylate in a ratio of 80:20. This material was reacted with methyl methacrylate and butyl methacrylate (93:7) in a ratio of 5.4:94.6 by suspension polymerization to form macroparticles. The resulting composite was a shapeable, generally tractable but somewhat sticky material curable to a Gardner impact value of 4.4 in-lbs.

EXAMPLE 7

The procedure of Example 6 was repeated but varying the pressure, temperatures, and times of the final blending to form the polymerizable composition. Surprising variations in performance and quality of the resulting products demonstrate the criticality of these parameters to the process.

| Run | Time | Temperature | Pressure | Gardner | Handleability |
|---|---|---|---|---|---|
| Example 6 | 22 min. | 52° C. | 85 mm Hg | 4.4 in-lbs | sticky, tractable |
| G. | 22 min. | 52° C | 30 mm | 2.8 in-lbs | stiff, intractable |
| H. | 22 min. | 52° C | 50 mm | 3.8 in-lbs | tractable between A & B |
| I. | 22 min. followed by 16 hrs. | 52° C 50° C | 30 mm 30 mm | 4.75 in-lb | tractable |

EXAMPLE 8

A denture base composition prepared generally in accordance with Example 6 was prepared from the following materials:

| | Weight % |
|---|---|
| Urethane dimethacrylate | 36.71 |
| 1,6-Hexanediol dimethacrylate | 2.39 |
| Camphoroquinone | 0.12 |
| N,N-Dimethylaminoethylneopentyl acrylate-methacrylic acid salt | 0.62 |
| Gamma-methacryloxypropyltrimethoxysilane | 0.15 |
| Butylated hydroxytoluene | 0.005 |
| Rubber-modified polymer | 45.58 |
| Fumed silica, Aerosil TM R972 | 14.38 |
| Red acetate fibers | 0.03 |

| | Weight % |
|---|---|
| Pigments | Trace |

Final mixing of the polymerizable composition was performed at 55° C. at 85 mm Hg pressure to form a tractable, visible light curable putty-paste having a cured Gardner impact value of 4.7 in-lbs (ASTM 3029-72), an elastic modulus of 527,000 psi (ASTM D-290-71) and a 13,400 psi modulus of rupture (ASTM D790-71). This value compares favorably with the composition of Example 1 (Gardner impact of 2.1 in-lbs).

EXAMPLE 9

The effect on impact strength of substituting for a portion of the rubber modified polymer of the composition of Example 8, a crosslinked polymer (methyl methacrylate-coethylene dimethacrylate 99.8:0.2),(0.2 percent XL polymer) was investigated.

| Run | Rubber Modified Polymer | 0.2% XL Polymer | Gardner Impact |
|---|---|---|---|
| Example 8 | 100% | 0% | 4.7 in-lb |
| J | 75 | 25 | 3.4 |
| K | 50 | 50 | 2.7 |
| L | 25 | 75 | 2.9 |
| Example 1 | 0 | 100 | 2.1 |

All percentages in this patent application are weight percents based on 100 percent of the final composition except where clearly indicated as percents of additive combinations or of recited compositions. Where indicated as a percent of recited compositions or components, it is meant that the materials recited in the series are to be apportioned among themselves to equal 100 percent when added up. Unless another meaning is clearly intended, compound is meant to define a specific chemical compound while composition is meant to define one or more compounds having a stated characteristic either singly or in combination. A composite composition is a composition including two or more compositions differing in stated characteristic. A polymerizable composition is one that can polymerize. As a general understanding, the polymerizable compositions of the present invention harden on polymerization, changing in most preferred instances from putties or paste to solids that have firm attributes of hardness or shape retaining character, generally having some rigidity with flexing ability.

While in accordance with the patent statutes what is at present considered to be the preferred embodiments of the invention have been described, it will be obvious to those skilled in the art that numerous changes and modifications may be made therein without departing from the invention, and it is therefore aimed in the appended claims to cover all such equivalent variations as fall within the true spirit and scope of the invention.

What is claimed is:

1. A polymerizable composition comprising:
   a) from about 10 to about 70 weight percent of multifunctional crosslinking composition that comprises at least about 50 percent oligomeric material;
   b) from about 3 to about 70 wight percent of polymer composition comprising crosslinked polymer in the form of discrete particles that are not swellable in said multifunctional crosslinking composition at 24° C., said particles have been swollen by imbibing said crosslinking composition at temperatures above about 39° C.

2. The polymerizable composition of claim 1 wherein said polymer composition particles are swollen by said multifunctional crosslinking composition.

3. The polymerizable composition of claim 1 wherein said polymerizable composition comprises at least about 10 weight percent rubber-modified polymer.

4. A polymerizable composition comprising:
   a) from about 10 to about 70 weight percent of a multifunctional crosslinking composition having at least about 50 percent oligomeric material having a molecular weigh of at least 250; and
   b) from about 3 to about 70 weight percent of a polymer composition comprising crosslinked polymer int e form of discrete particles that have been swollen by imbibing said crosslinking composition at temperatures above about 35° C. and below about 80° C., said particles are not swellable in said multi-functional crosslinking composition at 25° C.

5. The composition of claim 1 or 4 wherein said particles are adapted to form interpenetrating networks with said multifunctional crosslinking composition.

6. The composition of claim 1 or 4 wherein said particles have an average particle size of from about 0.001 micron to about 500 microns.

7. The composition of claim 1 or 4 further comprising at least about 10% by weight rubber-modified polymer comprising particles of an elastomer having a glass transition temperature below 0° C. and having average diameters less than about 5 microns.

8. The composition of claim 1 or 4 wherein said particles are swollen in said crosslinking composition for at least about 24 hours.

9. The composition of claim 1 or 4 wherein at least a portion of said multifunctional crosslinking composition is imbibed into said particles in an amount equal to at least 10 percent by weight of said particles.

10. The composition of claim 1 or 4 wherein said particles are swollen in said crosslinking composition at temperatures above about 40° C. and below about 80° C.

11. The composition of claim 1 or 4 wherein said oligomeric material has a molecular weight of at least 300.

12. The composition of claim 1 or 4 wherein said oligomeric material has a molecular weight of at lest 340.

13. A polymerizable composition comprising:
   a) from about 10 to about 70 weight percent of multifunctional cross-linking composition that comprises at least about 50 percent multifunctional cross-linking agent;
   b) from about 3 to about 70 weight percent of polymer composition comprising cross-lined polymer in the form of discrete particles that are not swellable in said multifunctional cross-linking composition at 24° C., said particles have been swollen by imbibing said cross-linking composition at temperatures above about 39° C.

14. The polymerizable composite composition of claim 13 wherein said polymer composition particles are swollen by said multifunctional cross-linking composition.

15. The polymerizable composite composition of claim 13 wherein said polymer composition comprises at least 10 weight percent rubber-modified polymer.

16. The composition of claim 13 wherein said cross-linking agent is a compound of the general formula:

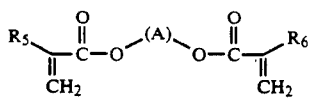

where $R_5$ and $R_6$ may be the same or different and are hydrogen or alkyl groups containing from 1 to about 6 carbon atoms and A is an aromatic moiety selected from the group consisting of (a) biphenyl, diphenyl alkylidene having from 1 to about 6 carbon atoms in the alkylidene portion thereof, diphenyl sulfone, diphenyl sulfoxide, diphenyl ether, and diphenyl sulfide; (b) the diglycidyl derivatives of group (a); and (c) a diurethane derivative of either group (a) or group (b), a glycidyl acrylate, allyl acrylate, divinyl benzene, trivinyl benzene or substituted divinyl benzene.

17. The composition of claim 13 wherein said cross-linking agent is an ester of a mono- or dibasic unsaturated acid with an unsaturated monohydroxylic alcohol.

18. The composition of claim 13 wherein said cross-linking agent is an allyl acrylate, allyl methacrylate, vinyl acrylate, vinyl methacrylate, dimethallyl fumarate, N-allyl acrylamide, crotyl acrylate, allyl crotonate, allyl cinnamate, diallyl maleate, di-, tri, and higher ester of polyhydroxylic alcohols, trimethyloipropane trimethacryalte, diacrylate and dimethacrylate ester of bisphenol-A acrylate or alkyl acrylate ester of the general formula:

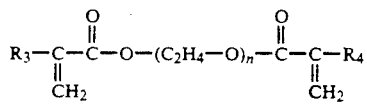

where $R_3$ and $R_4$ may be the same or different and are hydrogen or alkyl having from 1 to about 6 carbon atoms and n is a integer from 1 to about 10.

19. A polymerizable composition comprising:
a) from about 10 to about 70 weight percent of a multifunctional crosslinking composition having at least about 50 percent multifunctional cross-linking agent having a molecular weight of at lest 250; and
b) from about 3 to about 70 weight percent of a polymer composition comprising cross-linked polymer in the form of discrete particles that have been swollen by imbibing said cross-lining composition at temperatures above about 35° C. and below abut 80° C., said particles are not swellable in said multifunctional cross-linking composition at 24° C.

20. The composition of claim 19 wherein said particles are adapted to form interpenetrating networks with said multifunctional cross-linking composition.

21. The composition of claim 19 wherein said particles have an average particle size of form about 0.001 micron to about 500 microns.

22. The composition of claim 19 further comprising at least about 10% by weight rubber-modified polymer comprising particles of an elastomer having a glass transition temperature below 0° C. and having average diameters less than about 5 microns.

23. The composition of claim 19 wherein said particles are swollen in said cross-linking composition of at least about 24 hours.

24. The composition of claim 19 wherein at least a portion of said multifunctional cross-linking composition is imbibed into said particles in an amount equal to at least 10 percent by weight of said particles.

25. The composition of claim 19 wherein said particles are swollen in said cross-linking composition at temperatures above about 40° C. and below about 80° C.

26. The composition of claim 19 wherein said oligomeric material has a molecular weight of at least 300.

27. The composition of claim 19 wherein said oligomeric material has a molecular weight of at least 340.

28. The composition of claim 19 wherein said particles are adapted to form interpenetrating networks with said multifunctional cross-linking composition.

29. The composition of claim 13 wherein said particles have an average particle size of from about 0.001 micron to about 500 microns.

30. The composition of claim 13 further comprising at least about 10% by weight rubber-modified polymer comprising particles of an elastomer having a glass transition temperature below 0° C. and having average diameters less than about 5 microns.

31. The composition of claim 13 wherein said particles are swollen in said cross-linking composition for at least about 24 hours.

32. The composition of claim 13 wherein at least a portion of said multifunctional cross-linking composition is imbibed into said particles in an amount equal to at least 10 percent by weight of said particles.

33. The composition of claim 13 wherein said particles are swollen in said cross-linking composition at temperatures above about 40° C. and below about 80° C.

34. The composition of claim 13 wherein said oligomeric material has a molecular weight of at least 300.

35. The composition of claim 13 wherein said oligomeric material has molecular weight of at least 340.

* * * * *